United States Patent [19]

Uhrig et al.

[11] Patent Number: 5,440,060

[45] Date of Patent: Aug. 8, 1995

[54] SURFACE-ACTIVE COMPOUNDS BASED ON ALKOXYLATED FATTY AMINES

[75] Inventors: Heinz Uhrig, Steinbach/Taunus; Albert Münkel, Liederbach, both of Germany

[73] Assignee: Hoechst AG, Frankfurt, Germany

[21] Appl. No.: 114,388

[22] Filed: Aug. 30, 1993

[30] Foreign Application Priority Data

Aug. 29, 1992 [DE] Germany .................. 42 28 871.1

[51] Int. Cl.$^6$ .......................................... C07C 101/80
[52] U.S. Cl. .................................. 559/107; 560/88; 560/91; 560/196; 560/221; 560/251; 564/511; 564/512; 564/505; 568/579; 568/583; 568/606; 568/607
[58] Field of Search ............... 554/107; 560/88, 91, 560/196, 221, 207; 564/511, 512, 505; 568/519, 583, 606, 607

[56] References Cited

U.S. PATENT DOCUMENTS

| | | | |
|---|---|---|---|
| 3,028,415 | 4/1962 | Nordgren | 260/465.5 |
| 3,615,797 | 10/1971 | Ohtsuka et al. | 106/278 |
| 4,341,716 | 7/1982 | Diery et al. | 260/465 |
| 4,385,901 | 5/1983 | Podder | 8/527 |
| 4,416,808 | 11/1983 | Blaschke et al. | 252/547 |
| 4,701,284 | 10/1987 | Hendricks et al. | 260/513 |
| 4,705,889 | 11/1987 | Hendricks et al. | 562/564 |
| 4,713,482 | 12/1987 | Töpfl et al. | 560/196 |
| 4,778,919 | 10/1988 | Töpfl | 560/85 |
| 4,929,309 | 5/1990 | Bachem et al. | 162/164.3 |
| 4,939,238 | 7/1990 | Uhrig et al. | 530/212 |
| 4,997,912 | 3/1991 | Wirtz et al. | 554/109 |
| 5,082,527 | 1/1992 | Bachem et al. | 162/164.3 |
| 5,093,470 | 3/1992 | Bachem et al. | 528/407 |
| 5,372,747 | 12/1994 | Uhrig et al. | 252/356 |

FOREIGN PATENT DOCUMENTS

| | | |
|---|---|---|
| 0025998 | 5/1983 | European Pat. Off. . |
| 0042355 | 4/1984 | European Pat. Off. . |
| 0196596 | 10/1986 | European Pat. Off. . |
| 0296543 | 12/1988 | European Pat. Off. . |
| 0197005 | 1/1989 | European Pat. Off. . |
| 0195328 | 2/1989 | European Pat. Off. . |
| 0320769 | 6/1989 | European Pat. Off. . |
| 0335157 | 10/1989 | European Pat. Off. . |
| 0335158 | 10/1989 | European Pat. Off. . |
| 0341593 | 11/1989 | European Pat. Off. . |
| 0235088 | 12/1989 | European Pat. Off. . |
| 2623218 | 5/1989 | France . |
| 3145734 | 5/1983 | Germany . |
| 2220215 | 1/1990 | United Kingdom . |

OTHER PUBLICATIONS

Kirk-Othmer *Encyclopedia of Chemical Technology*, 4th Ed., vol. 6, 1965, pp. 634–640.
Bruson, H. A., *Cyanoethylation*, "Organic Reactions", N.Y., John Wiley and Sons, 1949, pp. 79–135.

*Primary Examiner*—Jose G. Dees
*Assistant Examiner*—Deborah D. Carr
*Attorney, Agent, or Firm*—Connolly & Hutz

[57] ABSTRACT

The demands on the properties of pigments, in particular in the areas of emulsion paints and printing inks, which are continuously becoming more specific made it necessary to develop selective and environmentally safe dispersing and emulsifying agents and coupling auxiliaries.

The compounds according to the invention are alkoxylation products prepared from fatty amine dialkylenediamines which, if desired, are linked to give recurring structural units by means of esterification with dicarboxylic acids and in which, preferably, the hydroxyl end groups of these fatty amine alkylenediamine alkoxylates have been esterified with fatty acids, aromatic carboxylic acids and/or resin acids and any hydroxyl groups still present have been converted to the corresponding mono-ester-containing anionic radicals by means of dicarboxylic acids and sulfites.

The compounds according to the invention are suitable for a wide range of areas of application in the surfactant sector, for example in the preparation of azo pigments, emulsion paints and printing inks, for the improvement of coloristic and rheological properties. The compounds according to the invention are particularly environmentally safe owing to their biodegradability.

15 Claims, No Drawings

SURFACE-ACTIVE COMPOUNDS BASED ON ALKOXYLATED FATTY AMINES

BACKGROUND OF THE INVENTION

1. Field of the Invention

The invention is in the area of surface-active agents.

2. Description of the Prior Art

When dispersions and preparations of colorants, for example disperse dyes, in particular of inorganic and organic pigments, are produced, a multiplicity of nonionic, anionic and also cationic surfactants are used for applications in aqueous and organic media. The type of surfactants exerts a substantial influence on fine dispersion and, accordingly, on the color strength of the colorants in the particular application media. Moreover, viscosity, gloss and shelf life are greatly influenced by the type of surfactants. In the preparation of azo pigments and azo dyes, surfactants are usually also used for a smoother course of the coupling reaction and for the preparation of colorants. The continuously increasing demands on the coloristic and rheological properties of azo pigments make it necessary, in particular in the area of printing inks, to selectively develop preparing agents which improve the flowability of printing inks.

U.S. Pat. No. 4,341,716 and U.S. Pat. No. 4,385,901 describe polyether polyamines and dialkyl sulfosuccinates and sulfuric esters based on alkoxylated fatty amines containing 12 to 22 carbon atoms in the fat moiety for the preparation of readily flowable pigment dispersions and for the preparation of easily dispersible dye preparations.

In U.S. Pat. No. 4,705,889 and U.S. Pat. No. 4,713,482 bis($\omega$-aminoalkyl)alkylamines are reacted with maleic acid to give the monoamide, and the resulting product is used as a neutral salt for emulsification in the preparation of polymer dispersions. Maleic and phthalic monoesters of alkoxylated fatty amines are used for the dyeing of wool-containing fiber materials.

In U.S. Pat. No. 4,778,919, maleic and phthalic monoesters of alkoxylated fatty amines are used as leveling agents.

Furthermore, in U.S. Pat. Nos. 4,929,309 and 5,082,527 and 5,093,470, nitrogen-containing, water-soluble polymers obtainable by reaction of the reaction product containing halohydrin groups with inorganic bases, followed by reaction of the resulting epoxy compounds with halogen-free sulfonic acids to give sulfonic esters are used for enhancing the wet strength of paper.

In U.S. Pat. No. 4,416,808, bisbetaines based on alkoxylated fatty amine alkylenediamines are used as personal care treatments.

However, none of the products described in the above-mentioned printed publications is suitable for decisively improving the course of the coupling reaction and the preparation of azo colorants associated therewith with respect to flowability of printing inks and for finely dispersing and stabilizing sparingly soluble or insoluble pigments without adversely affecting other parameters, such as color strength, gloss or hue.

SUMMARY OF THE INVENTION

The object of the present invention was to provide novel surface-active agents which are suitable for the preparation of readily flowable, mineral-oil-compatible solid dispersions which have high color strength and are resistant to flocculation, preferably colorant dispersions, for printing inks, for mass coloration of paper and, if desired, for exterior painting and are substantially free of the abovementioned disadvantages.

DESCRIPTION OF THE PREFERRED EMBODIMENTS

The present invention relates to novel compounds of the formula (I)

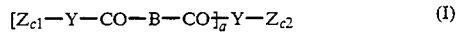

in which a is a number from 0 to 9, preferably 1 to 4;

c1 and c2 are identical or different and a number from 4 to 22, preferably 6 to 12;

each Y is a unit of the formula (Ia) which is identical to or different from that of the other Y radicals

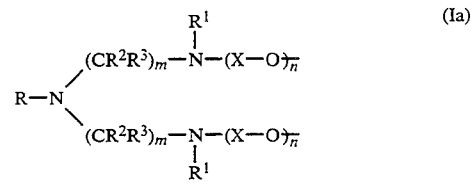

in which

X is a group of the formulae $-CH_2CH_2-$, $-CH(CH_3)CH_2-$ and $-CH_2-CH(CH_3)-$ or a combination thereof;

R is a saturated or unsaturated straight-chain or branched $C_{12}-C_{22}$-alkyl radical, $R^1$ is a hydrogen atom or a divalent group of the formula $-(X-O)_n-$ $R^2$ and $R^3$ are identical or different and are a hydrogen atom or a methyl group, preferably a hydrogen atom, m is a number from 2 to 3, preferably 3, and each n is a number from 1 to 200 which can be identical to or different from that of the other n, preferably 1 to 50, in particular 5 to 30;

each Z is a radical selected from $Z^1$ to $Z^7$ which is identical to or different from that of the other Z, in which $Z^1$ is hydrogen, $Z^2$ is an acyl radical of a straight-chain, saturated or unsaturated $C_2-C_{22}$-carboxylic acid, preferably $C_8-C_{20}$-carboxylic acid, which is unsubstituted or substituted by one or two hydroxyl groups, $Z^3$ is an acyl radical of a di- or tricarboxylic acid based on a di- or trimerized $C_8-C_{24}$-fatty acid, $Z^4$ is an acyl radical of the formula $R^4-CO-$, in which $R^4$ is a phenyl, naphthyl, hydroxyphenyl or hydroxynaphthyl radical, $Z^5$ is an acyl radical of an unmodified or modified natural resin acid, $Z^6$ is a radical of the formulae $-CO-CH=CH-COOM$, $-CO-(CH_2)_q-COOM$, $-CO-CH_2-CH(SO_3M)-COOM$, $-CO-CH(SO_3M)-CH_2-COOM$, $-OC-C_6H_4-COOM$ which is identical to or different from that of the other $Z^6$, in which q is an integer from 0 to 10, preferably from 2 to 4, and $Z^7$ is $-SO_3M$, in which M is hydrogen; an alkali metal; one equivalent of an alkaline earth metal; an oxyalkyl radical of the formula $(X-O-)_nH$; an ammonium group which is unsubstituted or substituted by one to four $C_1$–$C_5$-alkyl radicals or one to four $C_2$–$C_5$-alkylol radicals; an ammonium group obtained from ammonia or from $C_1$–$C_5$-alkylamines or $C_2$–$C_5$-alkylolamines by an addition reaction with 1 to 150, preferably 5 to 30, ethylene oxide or propylene oxide units or a combination of ethylene oxide and propylene oxide units; or a group of the formula (II)

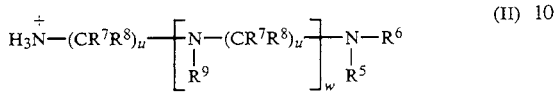
(II)

in which $R^9$, $R^5$ and $R^6$ are identical or different and are a hydrogen atom or a hydroxyalkyl group having 1 to 6 carbon atoms, preferably 2 to 3 carbon atoms, and $R^7$ and $R^8$ are identical or different and are hydrogen or methyl, each u is identical to or different from the others and is an integer from 2 to 14, preferably 2 to 3, and w is an integer from zero to 25, preferably from zero to 5; or in which M is a group of the formula (III)

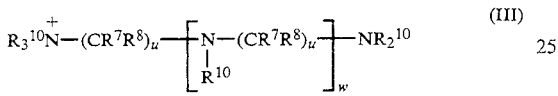
(III)

in which
$R^{10}$ is the group H—(O—X—)$_y$, in which X has the abovementioned meanings and y is an integer from 1 to 100, preferably 1 to 30, and
B is a straight-chain, branched or cyclic aliphatic radical each having 1 to 60 carbon atoms, preferably 1 to 30 carbon atoms, and is in particular straight-chain $C_1$–$C_8$-alkylene, $C_6$–$C_{12}$-arylene or a group of the formulae —CH=CH—, —CH(SO$_3$M)CH$_2$— or —CH$_2$CH(SO$_3$M)—, in which M is a cation or a radical of the formula —(X—O—)$_n$H;
and at least one radical Z being a radical from the group comprising $Z^2$, $Z^3$, $Z^4$, $Z^5$ and $Z^6$; or at least two units of the formula (Ia) being linked to one another via a divalent group —CO—B—CO— and Z having the meaning of $Z^1$ to $Z^7$.

Of particular interest are compounds of the formula (I), in which
a is a number from 1 to 4;
c1 and c2 are identical or different and are a number from 6 to 12.

Of particular interest are compounds of the formula (I), in which
R is a saturated or unsaturated straight-chain or branched $C_{12}$–$C_{18}$-alkyl radical;
X is a group of the formula —CH$_2$CH$_2$— for 50 to 100%, preferably 80 to 100%, of all radicals X and is a group of the formulae —CH(CH$_3$)CH$_2$— or —CH$_2$—CH(CH$_3$)— for 0 to 50%, preferably 0 to 20%, of all radicals X;
B is $C_1$–$C_6$-alkylene, 1,2-, 1,3- or 1,4-phenylene, a group of the formulae —CH=CH—, —CH(SO$_3$M)CH$_2$— or —CH$_2$CH(SO$_3$M)—, in which M is a cation,
m is the number 3 and
n is a number from 1 to 50, preferably 5 to 30, which is identical to or different from that of the other n.

Particular preference is given to compounds of the formula (I) in which 20 to 100%, preferably 30 to 70%, of the radicals Z, in each case independently of one another, have the meaning of the $Z^2$, $Z^3$, $Z^4$, $Z^5$, $Z^6$ or a combination thereof and 80 to 0%, preferably 70 to 30%, of the radicals Z have the meaning of $Z^1$, $Z^2$, $Z^4$, $Z^5$ or a combination thereof.

Of particular interest are furthermore compounds of the formula (I) in which a is a number from 1 to 4 and Z has the meaning of $Z^1$.

The present invention also provides a process for the preparation of a compound according to the invention of the formula (I), which comprises
a) alkoxylating an alkylaminodialkylenediamine on which the formula (Ia) is based with ethylene oxide or propylene oxide or both epoxides in succession or a mixture of both epoxides,
b) subsequently completely esterifying or partially esterifying the alkoxylate of the formula (Ia) obtained in step a)
b1) with at least one carboxylic acid on which the acyl radical $Z^2$, $Z^3$, $Z^4$, $Z^5$, $Z^6$ and —OC—B—CO— is based or a reactive derivative of this carboxylic acid, preferably an anhydride, in one or more steps or subjecting it to mixed esterification with a plurality of the abovementioned carboxylic acids or reactive derivatives thereof,
b2) and reacting, if desired, any maleic monoester groups present with a sulfite or sulfurous acid,
b3) if desired, sulfating the alkoxylate obtained by a) by means of a sulfating agent on which the radical $Z^7$ is based, preferably sulfuric acid, chlorosulfonic acid, sulfamic acid or sulfur trioxide; and
c) in the case where a radical of the formula $Z^6$ or $Z^7$ has been introduced in b), converting, if desired, the product into the corresponding salt or alkoxylates using a base on which the radical M is based.

The alkylaminodialkylenediamines on which the formula (Ia) is based are obtained, for example, by reacting a primary amine of the formula R—NH$_2$ with a reactive nitrile of 2 to 3 carbon atoms (including the CN group) to give a compound of the formula (II)

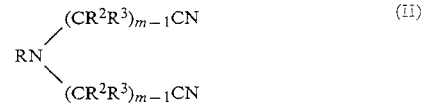
(II)

in a dicyanoalkylation reaction. This reaction is disclosed, for example, in U.S. Pat. No. 3,028,415. It can be carried out not only with acid but also with basic catalysis, by means of solvents, such as water or else low-chain alcohols in the absence of pressure or under elevated pressure, continuously or batchwise. Examples of suitable acid catalysts are acetic acid, phosphoric acid, hydrochloric acid or other mineral acids (U.S. Pat. No. 3,615,797, U.S. Pat. No. 3,028,415), and examples of suitable basic catalysts are sodium hydroxide or potassium hydroxide, alkali metal alcoholates, trimethylbenzylammonium hydroxide or morpholine (Kirk-Othmer, Encyclopedia of Chemical Technology, 1965, volume 6, page 634 ff.; H. A. Bruson "Cyanoethylation", Organic Reactions 5, 1949, page 79 ff.; published by John Wiley and Sons, New York). Water or lower alcohols, such as methanol, ethanol, isopropanol or mixtures thereof, are added as co-catalysts or else as solubilizers in amounts of 1 to 20% by weight. Dicyanoalkylation is carried out under atmospheric pressure or slight to medium overatmospheric pressure 1 to 20 bar, if desired in the presence of an inert gas, and at temperatures of 60° to 150° C. The cyanoalkylating agent, preferably acrylonitrile or chloroacetonitrile, is used in a stoichiometric amount or in an up to four-fold excess.

This is followed by reduction of the dicyanoalkylation product of the formula (II) in the presence of hydrogen to a compound of the formula (III)

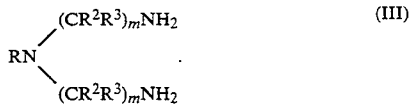

(III)

The reduction is carried out using Raney nickel, Raney cobalt or supported nickel catalysts or cobalt catalysts, using 1 to 10% by weight of catalyst, preferably 1 to 5% by weight, relative to the compound of the formula (III), at a pressure ranging from 50 to 200 bar of hydrogen and at temperatures of 60° to 150° C.; the reaction time of this reduction is about 1 to 5 hours.

Examples of amines of the formula R—NH$_2$ which are of interest are: coconut fatty amine, palm kernel fatty amine, tallow fatty amine, stearylamine, laurylamine, oleylamine or mixtures of the fatty amines mentioned.

a) Alkoxylation of the fatty amine alkylenediamines of the formula (III) can take place by customary methods. Preferably, the particular fatty amine alkylenediamine is reacted at a temperature of 100° to 200° C., preferably at 120° to 160° C., alternately with ethylene oxide or propylene oxide or both epoxides or as a mixture in the presence of a hydroxide or an alkoxide as the catalyst, preferably of an alkali metal hydroxide, such as potassium hydroxide or, in particular, sodium hydroxide, or of an alkali metal alkoxide, such as sodium methoxide or sodium ethoxide. The amount of the epoxides used or of the epoxide mixture is such that per reactive hydrogen atom of the free amino groups of the particular fatty amine alkylenediamine, 1 to 200, preferably 1 to 50, in particular 5 to 30, mol of the epoxide or epoxides used add to the fatty amine alkylenediamine. The concentration of the catalyst is preferably 0.05 to 1.0% by weight, relative to the fatty amine alkylenediamine, at the beginning of alkoxylation. A catalyst is not required if it is desired that preferably only one ethylene oxide or propylene oxide unit per chain adds to the fatty amine alkylenediamine. Alkoxylation can be carried out in the absence of pressure or in pressure vessels with propylene oxide or with ethylene oxide or with mixtures of both epoxides, it being possible for the alkylene oxide to be introduced in gaseous or liquid form. As a rule, the working pressure is 1 to 10 bar, preferably 2 to 8 bar. Depending on the intended use and the desired degree of hydrophilicity of the compounds of the formula (I) prepared from the alkoxylation products, the amount of the alkylene oxide which adds to the fatty amine alkylenediamine can be varied and optimized.

b) Esterification of the fatty amine alkylenediamine alkoxylates of the formula (Ia) takes place in one or more reaction steps, the radical Z having the meaning $Z^2$, $Z^3$, $Z^4$, $Z^5$ and $Z^6$ being usually introduced by reaction with the corresponding carboxylic acids, dicarboxylic acids, esters thereof or anhydrides thereof.

b1) In this manner, some or all hydroxyl groups of the fatty amine alkylenediamine alkoxylates can be esterified with the abovementioned carboxylic acids or derivatives thereof. Esterification takes place in a fatty amine alkylenediamine alkoxylate/carboxylic acid (derivative) molar ratio in the range from 1:1 to 1:4. It is also possible to use mixtures of the abovementioned carboxylic acids or the derivatives thereof. In most cases, it is advantageous to esterify in a first reaction step a portion of the hydroxyl groups present with monofunctional carboxylic acids and then to esterify the resulting product in a second reaction step with dicarboxylic acids, the second reaction step resulting, depending on the amount of dicarboxylic acid used, in introduction of anionic radicals in the form of free carboxylate groups or, in particular if less than a stoichiometric amount of dicarboxylic acid is used, linkage of 2 to 10 units of the compounds of the formula (Ia) via a divalent radical —OC—B—CO— takes place.

Examples of acids on which the acyl radical $Z^2$ is based are acetic acid, propionic acid, butyric acid, valeric acid, caproic acid, heptanoic acid, octanoic acid, pelargonic acid, capric acid, undecanoic acid, lauric acid, tridecanoic acid, myristic acid, pentadecanoic acid, palmitic acid, heptadecanoic acid, stearic acid, nonadecanoic acid, arachidic acid, behenic acid, 10-undecenoic acid, lauroleic acid, myristoleic acid, palmitoleic acid, 6c- and 6t-octadecenoic acid, elaideic acid, oleic acid, linoleic acid, linolenic acid, ricinoleic acid or ricinenic acid, in particular even-numbered fatty acids or hydroxy fatty acids each having 8 to 20 carbon atoms, for example the abovementioned even-numbered fatty acids and in particular mixtures thereof obtained from natural products, such as tall oil fatty acid, tallow fatty acid, coconut oil fatty acid, palm oil fatty acid, linseed oil fatty acid, castor oil fatty acid and ricinenic acid, particularly preferably the fatty acids mentioned containing 12 to 18 carbon atoms and mixtures thereof.

The di- or tricarboxylic acids on which the acyl radical $Z^3$ is based are dimerized or trimerized fatty acids having 28 to 72, in particular 36 to 54, carbon atoms.

Examples of acids or anhydrides on which the acyl radical $Z^4$ is based are benzoic acid, salicylic acid, o-, m- and p-methylbenzoic acids, naphthoic acids, in particularly hydroxy-naphthoic acids, for example 3-hydroxy-1-naphthoic acid, 3-hydroxy-2-naphthoic acid, 4-hydroxy-2-naphthoic acid, 5-hydroxy-1-naphthoic acid, 5-hydroxy-2-naphthoic acid, 6-hydroxy-2-naphthoic acid and 7-hydroxy-2-naphthoic acid.

The resin acids on which the acyl radical $Z^5$ is based are unmodified or modified natural resin acids of the rosin type or reactive derivatives thereof, preferably resin acids, such as abietic acid, dehydroabietic acid, tetrahydroabietic acid, levopimaric acid, dextropimaric acid or isodextropimaric acid such as are present in commercially available rosin types, and modified resin acids, such as disproportionated, hydrogenated and dimerized natural resin acids.

Examples of acids or carboxylic anhydrides on which the acyl radical $Z^6$ is based are maleic acid, maleic anhydride, fumaric acid, phthalic acid, phthalic anhydride, isophthalic acid, terephthalic acid, oxalic acid, malonic acid, succinic acid, succinic anhydride, glutaric acid, glutaric anhydride, adipic acid, pimelic acid, suberic acid, azelaic acid, sebacic acid and sulfosuccinic acid, preferably succinic acid, phthalic acid, terephthalic acid, maleic acid and fumaric acid, in particular sulfosuccinic acid.

Esterification of the fatty amine alkylenediamine alkoxylates of the formula (Ia) with the abovementioned carboxylic acids or dicarboxylic acids and linkage of two or more fatty amine alkylenediamine alkoxylates of the formula (Ia) can take place by esterification methods customary per se. The reaction temperature to be maintained is usually between room temperature and 240° C., depending on the esterification method. In order to increase the yield, esterification is preferably carried out in an inert organic solvent which is suitable as entrainer for removing the water of reaction. For example, esterification can be carried out in xylene as the organic solvent and in the presence of acid catalysts at a temperature of 130° to 220° C. Examples of possible acid catalysts are acids and Lewis acids, such as benzenesulfonic acid, p-toluenesulfonic acid, boric acid, tin powder, zinc chloride or sulfuric acid. Tin powder is used in an amount of 1 to 4% by weight, and the remaining acids mentioned in an amount of 0.1 to 2% by weight, preferably 0.5 to 1% by weight, in each case relative to the compound to be reacted. In the case of the anhydrides of the acids mentioned, esterification takes place by mixing and stirring at 10° to 120° C., preferably at 40° to 80° C., in the presence of alkali metal hydroxides. The alkali metal hydroxide concentration is advantageously 0.1 to 1.0% by weight, relative to the total mixture. Introduction of anionic groups preferably takes place by esterification with maleic anhydride or phthalic anhydride by mixing and stirring at 20° to 100° C., preferably at 40° to 80° C., in the presence of alkali metal hydroxides. The alkali metal hydroxide concentration is preferably 0.1 to 1.0% by weight, relative to the total mixture. In the case of maleic anhydride, it is advantageous, owing to its tendency to sublimation, to work in pressure vessels under a superatmospheric pressure of 0.2 to 1 bar of nitrogen or air and to provide for vigorous mixing, since the melted maleic anhydride is sparingly miscible with a partially esterified alkoxylate at the beginning of the reaction.

Alternatively, esterification of the alkoxylated fatty amine alkylenediamine with the resin acids, fatty acids or aromatic carboxylic acids mentioned can also be effected by transesterification using the corresponding alkyl esters, preferably methyl esters, of the acids mentioned in the presence of 0.1 to 1.0 mol equivalents of alkoxide, preferably sodium methoxide, at 150° to 200° C., preferably 160° to 190° C., while distilling off the released alkanol, preferably methanol.

The nonionic fatty amine alkylenediamine alkoxylate resin esters, fatty amine alkylenediamine alkoxylate fatty acid esters or fatty amine alkylenediamine alkoxylate aromatic carboxylic esters according to the invention are as such useful surface-active agents and can be used for the purposes of the invention.

Linkage of a plurality of fatty amine alkylenediamine units of the formula (Ia) can be effected by reaction of the fatty amine alkylenediamine alkoxylates in a first reaction step by esterification with one or more dicarboxylic acids of the formula HOOC—B—COOH in a molar ratio of 2:1 to 10:9, preferably 2:1 to 5:4. Suitable dicarboxylic acids for this linkage are preferably aliphatic dicarboxylic acids having 3 to 32 carbon atoms, in particular malonic acid, maleic acid, succinic acid, glutaric acid, adipic acid, 1,5-pentanedicarboxylic acid, 1,6-hexanedicarboxylic acid or 1,10-decanedicarboxylic acid, but also, for example, cyclohexane-1,4-dicarboxylic acid and aromatic dicarboxylic acids, such as phthalic acid or terephthalic acid. Instead of the acids it is also possible to carry out the esterification with, if they exist, the anhydrides or reactive carboxylic acid derivatives, for example in the case of transesterification reactions with lower alkyl esters of carboxylic acids.

The linked fatty amine alkylenediamine alkoxylate units are themselves surface-active agents and can be used for the purposes of the invention. The linkage according to the invention of two or more fatty amine alkylenediamine units already esterified at their end group with monocarboxylic acids on one portion of the polyglycol ether chain can preferably be carried out in a second reaction step by esterification with one of the abovementioned dicarboxylic acids, the fatty amine alkylenediamine alkoxylate partial ester/dicarboxylic acid ratio being preferably again 2:1 to 10:9. In the case where the partially esterified block polymer has only one free hydroxyl group left, a molar ratio of about 2:1 is adequate.

The partial esters of these linked fatty amine alkylenediamine alkoxylate units too are surface-active agents and can be used for the purposes of the invention.

It is also possible to carry out the reaction of the fatty amine alkylenediamine alkoxylate with monocarboxylic acids and dicarboxylic acids in one reaction step, in which case mixtures of polynuclear and mononuclear esterified fatty amine alkylenediamine alkoxylates are usually formed.

b2) In the case where maleic monoester groups have been introduced, it is advantageous to convert these monoester groups into the corresponding sulfosuccinic monoester groups. This can be achieved, for example, by addition of aqueous sulfite, pyrosulfite or bisulfite solutions to the compounds containing maleic monoester groups. 1.0 to 1.5 mol, preferably 1.0 to 1.1 mol, of sulfurous acid are used in the form of alkali metal sulfites or alkaline earth metal sulfites or alkali metal bisulfites or alkaline earth metal bisulfites or alkali metal pyrosulfites or alkaline earth metal pyrosulfites per maleic monoester group. The amount of water added is usually about 50 to 85% by weight, relative to the total solution or mixture and depends on the solubility of the sulfosuccinic monoester salts and the viscosity of the solution. The reaction temperature during the reaction of the sulfites mentioned with the maleic monoester compounds is usually 20° to 100° C., preferably 40° to 80° C.

b3) In order to introduce $SO_3M$ groups, the alkoxylates obtainable by b) are reacted with 1 to 9 mol, preferably 1 to 4 mol, of a sulfating agent, for example sulfuric acid, sulfamic acid or chlorosulfonic acid, or the corresponding anhydrides, per mole of alkoxylate. While sulfation with sulfamic acid results in the formation of the ammonium salts of the sulfuric monoesters, the embodiment in which gaseous sulfur trioxide is used in mixtures with inert gas and also sulfation with chlorosulfonic acid gives sulfuric monoesters in the acid form, salts can be prepared in accordance with c) by neutralization with suitable inorganic or organic bases. The bases preferably used for this neutralization are alkali metal hydroxides, which lead to the highly water-soluble alkali metal salts of the sulfuric monoesters according to the invention.

An advantageous embodiment provides, in the preparation of mixed esters resin acids, fatty acids or aromatic carboxylic acids, on the one hand, and dicarboxylic acids on which the radical $Z^6$ is based, on the other. These mixed esters can be prepared as mentioned above by at least two successive partial esterification steps, esterification with the dicarboxylic acid (derivative) being advantageously the last partial esterification step.

c) In a preferred embodiment, the alkoxylation products containing 1 to 20, preferably 2 to 10, carboxyl groups or sulfo groups are neutralized with alkali metal hydroxides or alkaline earth metal hydroxides or, preferably, with bases, such as ammonia, $C_1$–$C_5$-alkylamines, $C_2$–$C_5$-alkylolamines or alkylene oxide adducts thereof, up to 150 mol of ethylene oxide or propylene oxide or a combination of both having added to each mole of amine or alkylolamine, or with amines of the formulae (II) or Examples of suitable alkylamines and alkylolamines are: ethylamine, propylamine, isopropylamine, n-butylamine, isobutylamine, monoethanolamine, monopropanolamine, monoisopropanolamine, monobutanolamine, monoisobutanolamine, diethanolamine, dipropanolamine, dibutanolamine, triethanolamine, tripropanolamine or tributanolamine and di- and polyamines, such as 1,2-diaminoethane, 1,3-diaminopropane, 1,2-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diaminododecane, diethylenetriamine, dipropylenetriamine, triethylenetetramine, dipropylenetetramine, tetraethylenepentamine, tetrapropylenepentamine, pentaethylenehexamine, pentapropylenehexamine, hexaethyleneheptamine, hexapropyleneheptamine, heptaethyleneoctamine, heptapropyleneoctamine, 1,3-diamino-2,2-dimethylpropane, 1,2-diamino-2-methylpropane, 1,3-diamino-2-methylpropane, 2,5-diamino-2,5-dimethylhexane, N-(2-aminoethyl)-1,3-propylenediamine and N,N'-bis(3-aminopropyl)ethylenediamine.

Owing to the large number of reactive centers in the starting compounds, the preparation of the compounds according to the invention does not give a pure uniform end product, rather a mixture, which however contains the compounds of the formula (I) as the main component, i.e. more than 50% by weight, preferably more than 90% by weight, thereof.

The process according to the invention provides mixtures in particular in those cases where an alkoxylate obtainable by reaction step a) is esterified in a single reaction step with a plurality of different carboxylic acids. If dicarboxylic acids are also present in this esterification, mixtures of bridged and unbridged alkoxylate esters are usually formed.

The molecular weight of the compounds according to the invention can vary within a wide range and ranges from 1000 to 20,000, preferably 2000 to 10,000, in particular 1000 to 5000.

The compounds according to the invention are yellowish or brownish, low-foaming surface-active substances which are surprisingly suitable for the preparation of readily flowable and stable solid dispersions, in particular of readily flowable pigment preparations which are resistant to flocculation.

The compounds according to the invention exhibit versatile advantageous properties. They belong to the class of surface-active compounds according to DIN (German Standard Specification) 53900, lower the surface tension as measured by the ring detachment method (DIN (German Standard Specification) 53914) and must be designated, according to the results in the modified Ross-Miles test (DIN (German Standard Specification) 53902) as non-foaming or low-foaming surface-active substances. If they exhibit a suitable degree of hydrophilicity, they show excellent wetting power for cotton as measured by the dip-wetting method (DIN (German Standard Specification) 53901) in combination with good leveling properties in accordance with DIN (German Standard Specification) 53504. They have very good flocculation-preventing power towards pigments and dyes (DIN (German Standard Specification) 53908) and a very good water-distributing effect as cleaning promoter (DIN (German Standard Specification) 53980) and good wash-off properties as yarn lubricant (DIN (German Standard Specification) 53504). The compounds according to the invention are biodegradable and thus particularly environmentally safe.

Owing to their versatile surface-active properties, the compounds according to the invention can be used for a broad spectrum of applications.

Accordingly, the invention also provides for the use of a compound of the formula (I) as a surface-active agent. Of particular interest is the use as coupling auxiliary and preparing agent for the preparation of azo colorants, in particular of azo pigments, preferably for the production of pigment preparations for the aqueous printing inks sector; as dispersing agent for fine dispersion and stabilization of solids, preferably sparingly soluble or insoluble, inorganic and organic colorants, preferably for the preparation of readily flowable pigment dispersions for aqueous emulsion paints; for the dyeing or pigmenting of leather; and for the formulation of disperse dyes, such as are preferably used for the dyeing of natural and synthetic fiber materials, such as cotton, wool, cellulose, staple viscose, cellulose acetate, cellulose triacetate, polyester, polyamide and polyacrylonitrile, or of fiber materials containing these substances.

The compounds according to the invention are also suitable for use as additives and emulsifiers, for example as anticorrosive additives and as additives for the preparation of cooling lubricants and cold-rolling oils in the metal-working industry. Furthermore, the substances can be used as dispersants and emulsifiers for the preparation of cleaning promoters, carrier emulsions and formulations for crop protection agents and pest control agents and as additives for spinning solutions and spinning baths. Furthermore, they are suitable as wetting, leveling, flotation, and viscose finishing agents, and as dyeing assistants.

The compounds according to the invention can be used individually or as mixtures and in combination with other, nonionic and, if desired, with anionic or cationic surfactants or mixtures thereof. Furthermore, they can be used together with customary amounts of builders or other customary additives or auxiliaries in formulations of emulsifying and dispersing agents.

In the examples which follow, "parts" and percentages are by weight, and parts by volume relate to parts by weight as the liter relates to the kilogram. The degree of conversion in the reaction steps described above is characterized in the Preparation Examples by the determination of the hydroxyl number, acid number and amine number. The acid number (AN) is determined by DIN (German Standard Specification) 53402). The acid number indicates the amount of potassium hydroxide in milligrams consumed for neutralization of 1 g of the reaction product. The hydroxyl number is determined by DIN (German Standard Specification) 53240) and is a measure of the free hydroxyl group content in the molecule; it corresponds to the amount of potassium hydroxide in mg necessary for neutralizing the amount of acetic acid consumed upon acetylation of 1 g of the test substance. The amine number is determined by DIN (German Standard Specification) 53176 and is that amount of potassium hydroxide in milligrams which is equivalent to the amine content of 1 g of substance.

Preparation Example 1 a) N-Tallow fatty amine dipropylenediamine alkoxylate 200 parts of N-tallow fatty amine dipropylenediamine were propoxylated with stirring and the addition of 187 parts of propylene oxide without addition of a catalyst while maintaining a pressure of 2 to 4 bar and a temperature of 130° to 140° C. After addition of 3.3 parts of 30% sodium methoxide in methanol and removal of the methanol under reduced pressure 474 parts of ethylene oxide were introduced at 120° to 140° C. and a pressure of 3 to 5 bar. After the entire ethylene oxide had been injected, the mixture was stirred at 140° to 150° C. for 1 hour. The highly viscous, yellow-brown alkoxylate obtained contained 6 propylene oxide units and 20 ethylene oxide units and has a hydroxyl number of 70.

b) N-Tallow fatty amine dipropylenediamine alkoxylate dirosin ester 300 parts of the alkoyate according to Preparation Example 1a) were heated together with 56.2 parts of disproportionated rosin, which corresponds to half the hydroxyl number, to 70° to 80° C. and stirred under nitrogen gas for one hour. After addition of 6 parts of tin powder, 2.0 parts of p-toluenesulfonic acid and 150 parts by volume of xylene, the mixture was heated at 15° to 160° C. for 16 hours, and the water of reaction was removed by azeotropic distillation. After the xylene had been distilled off, the product obtained had an acid number of less than 20.

Preparation Example 2

N-Tallow fatty amine dipropylenediamine alkoxylate dirosin ester dimaleic monoester diethylenetriamine salt 300 parts of rosin partial ester according to Preparation Example 1b) were monoesterified at 75° to 80° C. with 18.4 parts of maleic anhydride which corresponds to a residual hydroxyl number of 35, in the presence of 21 parts of powdered sodium hydroxide over a period of 4 hours, and, after obtaining an acid number of 46.6, the resulting product was neutralized at 60° to 70° C. with 28.7 parts of diethylenetriamine. The product obtained is water-soluble, has a pH of 8.9 to 9.2 in water and an amine number of 193.

Preparation Example 3

3a) N-Tallow fatty amine dipropylenediamine alkoxylate malonate 200 parts of N-tallow fatty amine dipropylenediamine were reacted with 126.8 parts of propylene oxide as described in Preparation Example 1a), and the resulting product, after addition of 3.3 parts of 30% sodium methoxide in methanol and removal of the methanol under reduced pressure, was ethoxylated with 572 parts of ethylene oxide. The highly viscous, yellow-brown alkoxylate obtained contains 4 propylene oxide and 24 ethylene oxide units at a hydroxyl number of 136.

600 parts of this alkoxylate were then heated at 70° to 80° C. under nitrogen gas together with 25 parts of malonic acid. After addition of 3 parts of p-toluenesulfonic acid and 200 parts by volume of xylene, the mixture was heated at 155° to 165° C. for 10 hours and the water of reaction was removed by azeotropic distillation. After the xylene has been distilled off the product has an acid number of less than 10, a hydroxyl number of 94.6 and contains 12 propylene oxide units and 72 ethylene oxide units per molecule.

3b) N-Tallow fatty amine dipropylenediamine alkoxylate malonate trirosin ester 300 parts of the alkoxylate according to Preparation Example 3a) were heated at 70° to 80° C. together with 57.3 parts of disproportionated rosin, which corresponds to ⅜ of the hydroxyl number, and the mixture was stirred under nitrogen gas for one hour. After addition of 6 parts of tin powder, 2.0 parts of p-toluenesulfonic acid and 150 parts by volume of xylene, the batch was heated at 150° to 160° C. for 16 hours and the water of reaction was removed by azeotropic distillation. After the xylene had been distilled off, the product obtained had an acid number of less than 15.

Preparation Example 4

N-Tallow fatty amine dipropylenediamine alkoxylate malonate trirosin ester pentasulfosuccinate 300 parts of the rosin partial ester according to Preparation Example 3b) were monoesterified at 75° to 85° C. with 95 parts of maleic anhydride, which corresponds to a hydroxyl number of 59, under nitrogen gas and then reacted with a solution of 122 parts of sodium sulfite in 960 parts of water at 75° to 80° C. over a period of 1 to 3 hours. After the batch had clarified, stirring was continued for another hour. The main product obtained is a sulfosuccinic monoester having a residual hydroxyl number of 6.3, in which all 5 polyoxyalkylene chains have been reacted at the end group.

Preparation Example 5

5a) Di(N-palm kernel fatty amine dipropylenediamine alkoxylate) phthalic ester 200 parts of N-palm kernel fatty amine dipropylenediamine were reacted with 126.5 parts of propylene oxide as described in Preparation Example 1a), and the resulting product, after addition of 3.3 parts of 30% sodium methoxide in methanol and removal of the methanol under reduced pressure, was ethoxylated with 761 parts of ethylene oxide. The highly viscous, yellow-brown alkoxylate obtained contains on average 4 propylene oxide and 32 ethylene oxide units per molecule at a hydroxyl number of 112.

300 parts of this alkoxylate were then reacted, after addition of 0.1 part of powdered sodium hydroxide at 110° to 120° C. with 22.1 parts of phthalic anhydride, which correspond to one fourth of the hydroxyl number, under nitrogen gas for 4 hours to give the phthalic monoester. The acid number found was 26.

A further 300 parts of N-palm kernel fatty amine dipropylenediamine alkoxylate and 1.5 parts of p-toluenesulfonic acid and 200 parts by volume of xylene were then added and esterification was carried out at 155° to 165° C. for 10 hours with removal of the water of reaction by azeotropic distillation. After the xylene had been distilled off, the product obtained had an acid number of 12 and a hydroxyl number of 80 to 82.

5b) Di(N-palm kernel amine dipropylenediamine alkoxylate) phthalic ester trirosin ester 300 parts of the alkoxylate according to Preparation Example 5a) were heated together with 65.4 parts of disproportionated rosin, which corresponds to half the hydroxyl number, to 70° to 80° C., and the mixture was stirred under nitrogen gas for one hour. After addition of 12 parts of tin powder, 4.0 parts of p-toluenesulfonic acid and 150 parts by volume of xylene, the mixture was heated at 150° to 160° C. for 16 hours, and the water of reaction removed by azeotropic distillation. After the xylene had been distilled off, the product obtained had an acid number of less than 18.

Preparation Example 6

N-palm kernel fatty amine dipropylenediamine alkoxylate rosin ester 1,3-propanediamine salt 300 parts of the rosin ester according to Preparation Example 5b) were reacted at 100° to 110° C. with 21.7 parts of succinic anhydride, which corresponds to a residual hydroxyl number of 40.5, under a stream of nitrogen for 4 hours until an acid number of 35.5 was reached to give the monoester, and the product obtained was neutralized in accordance with the acid number with 46.8 parts of 1,3-propanediamine. The amine salt obtained had a pH of 8 to 8.2 and an amine number of 82.

Preparation Example 7

7a) Di (N-coconut fatty amine dipropylenediamine alkoxylate) succinic ester 200 parts of N-coconut fatty amine dipropylenediamine were reacted with 310 parts of propylene oxide as described in Preparation Example 1a), and the resulting product, after addition of 3.3 parts of 30% sodium methoxide in methanol and removal of the methanol under reduced pressure, was alkoxylated with 571 parts of ethylene oxide. The highly viscous, yellow-brown alkoxylate obtained contains on average 8 propylene oxide and 44 ethylene oxide units per molecule at a hydroxyl number of 87. 300 parts of the alkoxylate obtained were monoesterified at 100° to 110° C. with 47.0 parts of succinic anhydride, which corresponds to ¼ of the hydroxyl number, over a period of 4 hours until an acid number of 65.7 was reached, and, after addition of 1.5 parts of p-toluenesulfonic acid and 322 parts of alkoxylate and 150 parts by volume of xylene, esterification was carried out at 155° to 165° C. for 10 hours with removal of the water of reaction by azeotropic distillation. After the water of reaction had been distilled off, a di(N-coconut fatty amine dipropylenediamine alkoxylate) linked via the —OC—CH$_2$—CH$_2$—CO— group and having an acid number of below 10 and a hydroxyl number of 64 was obtained.

7b) Di(N-coconut fatty amine dipropylenediamine alkoxylate) succinic ester hexarosin ester 300 parts of the alkoxylate according to Preparation Example 7a) were heated in accordance with the hydroxyl number together with 104 parts of disproportionated rosin to 70° to 80° C., and the mixture was stirred under nitrogen gas for one hour. After addition of 12 parts of tin powder, 4.0 parts of p-toluenesulfonic acid and 150 parts by volume of xylene, the resulting mixture was heated at 150° to 160° C. for 16 hours, and the water of reaction was removed by azeotropic distillation. After the xylene had been distilled off, the product obtained had an acid number of less than 20.

Preparation Example 8

8a) N-Tallow fatty amine dipropylenediamine alkoxylate 200 parts of N-tallow fatty amine dipropylenediamine were reacted with 250.1 parts of propylene oxide as described in Preparation Example 1a), and the resulting product, after addition of 3.3 parts of 30% sodium methoxide in methanol and removal of the methanol under reduced pressure, was ethoxylated with 1364 parts of ethylene oxide. The highly viscous, yellow-brown alkoxylate obtained contains on average 8 propylene oxide and 54.7 ethylene oxide units per molecule at a hydroxyl number of 69.4.

8b) N-Tallow fatty amine dipropylenediamine alkoxylate succinic monoester 500 parts of the alkoxylate according to Preparation Example 8a) were heated together with 15.5 parts of succinic anhydride, which corresponds to ¼ of the hydroxyl number, to 100° to 110° C. under nitrogen and thoroughly mixed. After addition of 0.1 part of sodium hydroxide the mixture was stirred in the same temperature range for 4 hours to give a product having an acid number of 16.7.

8c) Tri(N-tallow fatty amine dipropylenediamine alkoxylate) disuccinic ester 200 parts of the succinic monoester from Preparation Example 8b) were thoroughly mixed at 60° to 70° C. in accordance with the acid number with 193.3 parts of alkoxylate according to Preparation Example 8a) under nitrogen, and the resulting product, after addition of 3 parts of p-toluenesulfonic acid and 150 parts by volume of xylene, was esterified at 155° to 165° C. for 8 hours, during which the water of reaction was removed in a water separator by azeotropic distillation. The acid number of the product obtained is 8.9.

A further 208.6 parts of the alkoxylate succinic monoester according to Preparation Example 8b) were then added, and esterification at 155° to 165° C. was continued for another 8 hours with removal of the water of reaction. The xylene was then distilled off, and the acid number was determined. The product has an acid number of less than 5 and a hydroxyl number of 40 to 50. In the product obtained, 3 N-tallow fatty amine propylenediamine alkoxylate units according to Preparation Example 8a) are linked by 2 succinic acid units.

Preparation Example 9

Tri(N-tallow fatty amine dipropylenediamine alkoxylate) succinic ester benzoate sulfosuccinate 300 parts of the trialkoxylate according to Preparation Example 8c) were esterified, after addition of 2 parts of tin powder and 0.5 part of p-toluenesulfonic acid and 150 parts by volume of xylene, at 155° to 165° C. with 14.7 parts of benzoic acid, which corresponds to half the hydroxyl number, over a period of 12 hours with simultaneous removal of the water of reaction by azeotropic distillation. After the xylene had been distilled off, the resulting alkoxylate partially esterified with benzoic acid had an acid number of less than 20.

Esterification was then continued at 70° to 80° C. in the presence of 0.1 part of powdered sodium hydroxide and 11.8 parts of maleic anhydride for 3 to 4 hours, and the resulting product was then converted to the sulfur succinate at 75° to 80° C. over a period of 1 to 3 hours by addition of a solution of 15.2 parts of sodium sulfite and 634.6 parts of water. The product obtained is a sulfosuccinic monoester having a residual hydroxyl number of about 5.9, in which all 8 polyoxyalkylene groups have been reacted at the end groups.

Preparation Example 10

10a) N-Tallow fatty amine dipropylenediamine alkoxylate 200 parts of N-tallow fatty amine dipropylenediamine were alkoxylated analogously to Preparation Example 1a) with stirring and addition of 190 parts of propylene oxide and 1443.8 parts of ethylene oxide. The product obtained which is soft as butter contains 6 propylene oxide and 50 ethylene oxide units per molecule and has a hydroxyl number of 76.7.

10b) N-Tallow fatty amine dipropylenediamine alkoxylate tetraoleic ester 300 parts of the alkoxylate according to Preparation Example 10a) were esterified, after addition of 1.5 parts of p-toluenesulfonic acid and 150 parts by volume of xylene, at 155° to 165° C. in accordance with the hydroxyl number with 115.7 parts of commercially available oleic acid over a period of 12 hours with removal of the water of reaction by azeotropic distillation. After the xylene had been distilled off, a product having an acid number of less than 20 was obtained in which all 4 polyoxyalkylene groups have been esterified at the end groups.

Preparation Example 11

11a) N-Tallow fatty amine dipropylenediamine alkoxylate maleic monoester 500 parts of the alkoxylate according to Preparation Example 8a) were heated together with 15.1 parts of maleic anhydride, which corresponds to ¼ of the hydroxyl number, at 70° to 80° C. under nitrogen and thoroughly mixed. After addition of 0.1 part of sodium hydroxide, the mixture was stirred in the same temperature range for 4 hours to give a product having an acid number of 16.4.

11b) Tri (N-tallow fatty amine dipropylenediamine alkoxylate) maleic ester 200 parts of the maleic monoester according to Preparation Example 11a) were thoroughly mixed at 60° to 70° C. in accordance with the acid number with 189.8 parts of the alkoxylate according to Preparation Example 8a) in a nitrogen atmosphere. After addition of 3 parts of p-toluenesulfonic acid and 150 parts by volume of xylene, the product was esterified at 155° to 165° C. for 8 hours, during which the water of reaction was removed in a water separator by azeotropic distillation. This gave a product having an acid number of 8.5. A further 197.5 parts of the alkoxylate maleic monoester according to Preparation Example 11a) were then added, and esterification at 155° to 165° C. was continued for another 8 hours with removal of the water of reaction. The xylene was then distilled off, and the acid number was determined. The product had an acid number of less than 5 and a hydroxyl number of 40 to 50. In the product obtained, 3 N-tallow fatty amine dipropylenediamine alkoxylate units are linked by 2 maleic acid units.

11c) Tri(N-tallow fatty amine dipropylenediamine alkoxylate) dimaleic ester phthalic ester 1,3-propanediamine salt 200 parts of the trialkoxylate according to Preparation Example 11b) were heated to about 50° C., and 23.7 parts of phthalic acid, which corresponds to the hydroxyl number of the product present, were added in portions, and the mixture was stirred at 100° to 120° C. under nitrogen for 3 to 4 hours. This gave a yellow-brown, highly viscous phthalic monoester having an acid number of 44.3. After cooling to 55° to 65° C., the phthalic monoester was converted to the amine salt in accordance with the acid number by introducing 41.6 parts of 1,3-propanediamine and increasing the reaction temperature to 65° to 75° C. over a period of about 1 hour to give a yellow-brown amine product having an amine number of between 80 and 90.

Preparation Example 12

N-Tallow fatty amine dipropylenediamine alkoxylate dioleic ester disulfate 300 parts of the N-tallow fatty amine dipropylenediamine alkoxylate according to Preparation Example 10a) were esterified, after addition of 1.2 parts of p-toluenesulfonic acid and 150 parts by volume of xylene at 155° to 165° C. with 57.8 parts of commercially available oleic acid, which corresponds to half the hydroxyl number for 10 hours with removal of the water of reaction. After the xylene had been distilled off, esterification was continued at 170° to 180° C. for another 2 hours until an acid number of below 18 was reached.

The mixture was then diluted with 250 parts by volume of methylene chloride, and 47.8 parts of chlorosulfonic acid, which corresponds to the residual hydroxyl number, were added dropwise at 15° to 20° C., during which a gentle stream of dry nitrogen was passed through the solution, which removed the escaping hydrogen chloride gas via a reflux condenser. Towards the end of the reaction, the mixture was warmed to 30° C. and stirred until no more hydrogen chloride gas escaped. After the methylene chloride had been distilled off under reduced pressure at 30° C., 352 g of an oil having a titratable chlorine content of 0.04% remained as the residue. For neutralization, 900 parts of water were added, and the mixture was neutralized to a pH of 7.0 with 34.5 parts of 33% sodium hydroxide solution. The main product obtained is a sulfuric monoester having a residual hydroxyl number of 8.1 in which all 4 polyoxyalkylene chains have been converted at the end groups.

Preparation Example 13

13a) N-Tallow fatty amine dipropylenediamine alkoxylate 200 parts of N-tallow fatty amine dipropylenediamine were alkoxylated analogously to Preparation Example 1a) with stirring and addition of 253 parts of propylene oxide and 1443.8 parts of ethylene oxide. The product obtained which is soft as butter contains 8 propylene oxide and 50 ethylene oxide units per molecule and has a hydroxyl number of 70.0.

13b) Di(N-tallow fatty amine dipropylenediamine alkoxylate) dimeric fatty acid ester 371 parts of the alkoxylate according to Preparation Example 13a) were esterified, after addition of 2 parts of p-toluenesulfonic acid and 150 parts by volume of xylene, at 155° to 165° C. with 282 parts of commercially available dimeric fatty acid over a period of 8 hours, during which the water of reaction was removed in a water separator by azeotropic distillation. The xylene was then distilled off to give an acid number of 6.0. The product obtained contains 2 alkoxylate units linked by a dimeric fatty acid unit.

Preparation Example 14

14a) N-Tallow fatty amine dimethyldipropylenediamine alkoxylate 200 parts of N-tallow fatty amine dimethyldipropylenediamine were propoxylated at 130° C. to 140° C. with stirring and addition of 249 parts of propylene oxide without addition of a catalyst while maintaining a pressure of 2 to 4 bar. After addition of 3.3 parts of 30% sodium methoxide in methanol and removal of the methanol under reduced pressure, 474 parts of ethylene oxide were introduced at 120° to 140° C. and 3 to 5 bar.

After the entire ethylene oxide had been injected, the mixture was stirred at 140° to 150° C. for 1 hour. The highly viscous, yellow-brown alkoxylate obtained contains 8 propylene oxide and 20 ethylene oxide units per molecule and has a hydroxyl number of 65.

14b) N-Tallow fatty amine dimethyldipropylenediamine alkoxylate dirosin ester 300 parts of the alkoxylate according to Preparation Example 14a) were heated together with 52.5 parts of disproportionated rosin, which corresponds to half the hydroxyl number, to 70° to 80° C., and the mixture was stirred under nitrogen gas for 1 hour. After addition of 6 parts of tin powder, 2.0 parts of p-toluenesulfonic acid and 150 parts by volume of xylene, the mixture was heated at 150° to 160° C. for 16 hours and the water of reaction was removed by azeotropic distillation. After the xylene had been distilled off, the product obtained had an acid number of less than 18.

14c) N-Tallow fatty amine dimethyldipropylenediamine alkoxylate dirosin ester dimaleic monoester diethylenetriamine salt 300 parts of the rosin ester according to Preparation Example 14b) were monoesterified at 75° to 80° C. with 17 parts of maleic anhydride, which corresponds to a residual hydroxyl number of 32.5, in the presence of 21 parts of powdered sodium hydroxide over a period of 4 hours and, after reaching an acid number of 45.6, the resulting product was neutralized at 60° to 70° C. with 18.8 parts of diethylenetriamine. The product obtained is water-soluble and has a pH of 8.3 to 8.5 and an amine number of about 158.

Use Example 1

120.4 parts of 1-acetoacetylamino-2,4-dimethylbenzene and 12.2 parts of 1-acetoacetylamino-2,5-dimethoxy-4-chlorobenzene were dissolved in 1800 parts of water and 62 parts by volume of 33% sodium hydroxide solution, 3.0 parts of a fatty alcohol polyglycol ether were added, and the resulting product was precipitated by means of 22 parts by volume of acetic acid. After addition of 5.0 parts of the product from Preparation Example 2, the coupling reaction was effected by means of a solution of tetrazotized 4,4'-diamino-3,3'-dichlorobiphenyl, in which was prepared by addition of 120 parts by volume of aqueous 5-normal sodium nitrite solution to a mixture of 76 parts of 4,4'-diamino-3,3'-dichlorobiphenyl, 366 parts by volume of 5-normal hydrochloric acid and 1040 parts of water. After coupling was complete, 2.5 parts of dehydroabietylamine were added to the pigment suspension, the mixture was made alkyline, a solution containing 3.6 parts of the product from Preparation Example 7b) and 36 parts of a partially hydrogenated rosin was then added, and the reaction mixture was heated at 98° C. for 30 minutes. The pH was then brought to 4 with hydrochloric acid, and heating at 98° C. was continued for another 30 minutes. The reaction mixture was then filtered, and the product was washed and dried to give a pigment preparation which upon incorporation in a printing ink varnish for book and offset print gave a printing ink having very good technical application properties. The printing ink is distinguished by significantly improved flow behavior in combination with an increase in color strength and gloss compared with a printing ink prepared without addition of the products from Preparation Examples 2 and 7b).

Use Example 1a)

The products from Preparation Examples 2 and 7b) used in Use Example 1 were replaced by the products from Preparation Examples 6 and 11c. This gave a pigment preparation having properties similar to those described in Use Example 1.

Use Example 2

506 parts of 3,3'-dichloro-4,4'-diaminobiphenyl were stirred together with 3000 parts of water and 1250 parts by volume of 30% hydrochloric acid and then bisdiazotized at 0° to 15° C. with 526 parts by volume of 40% sodium nitrite solution. The coupling reaction was prepared by dissolving 733 parts of acetoacetylaminobenzene in 5000 parts of water and 400 parts by volume of 33% sodium hydroxide solution, adding 80 parts of the surfactant prepared according to Preparation Example 7b) and the resulting product was precipitated by addition of 350 parts by volume of 80% acetic acid. Azo coupling was carried out by slowly running in the bisdiazonium salt solution prepared to the suspension of the precipitated coupling component, during which the pH was maintained at about 4.5 by continuous addition of 6% sodium hydroxide. After coupling was complete, the acetic acid suspension was heated to 50° C., and 75 parts of dodecylbenzenedimethylammonium chloride, 375 parts of tallow fatty amine dipropylenediamine and 150 parts of bis(4-aminocyclohexyl)methane were added. The mixture was heated to 90° to 100° C., and this temperature was maintained for half an hour. The mixture was then made alkaline with 750 parts by volume of 33% sodium hydroxide solution and stirred at 90° to 100° C. for several hours. The product was then filtered, washed, dried and milled to give a C.I. Pigment Yellow 12 (C.I. No. 21090) preparation which is highly useful for the pigmenting of toluene-based gravure printing ink. The Pigment Yellow 12 preparation obtained gives very good results with respect to color strength, gloss, transparency and gradation behavior. The gravure printing inks pigmented therewith are also distinguished by an advantageous low viscosity. Similar results are obtained on using a combination of the compounds according to the invention from Preparation Examples 7b and 10b.

Use Example 3

1012 parts of 3,3'-dichloro-4,4'-diaminobiphenyl were stirred together with 6000 parts of water and 2500 parts by volume of 30% hydrochloric acid, and then bisdiazotized at 0° to 15° C. with 1052 parts by volume of 40% sodium nitrite solution. The coupling reaction was prepared by dissolving 1396 parts of 1-acetoacetylamino-2,4-dimethylbenzene and 341 parts of 1-acetoacetylamino-2-methoxybenzene in 10,000 parts of water and 830 parts by volume of 33% sodium hydroxide solution. This solution was brought to 10° C. with ice, and 40 parts by volume of a 10% solution of the 100% product from Preparation Example 2 were added. The coupling component was then precipitated with 1140 parts by volume of 50% acetic acid. Coupling was carried out by slowly running in the abovementioned bisdiazonium salt solution to the suspension of the precipitated coupling component, during which the pH was maintained at about 4.5 with 6% sodium hydroxide solution. After coupling is complete, 1100 parts by volume of 33% sodium hydroxide solution and a hot solution of 80° C. comprising 750 parts of a balsamic resin, 4000 parts by volume of water and 220 parts by volume of 33% sodium hydroxide solution were added to the pigment suspension. The reaction mixture was heated to 98° C., this temperature maintained for 2 hours, and 2000 parts by volume of 1-normal hydrochloric acid were then added. The product was then filtered, washed and dried.

This gave a pigment preparation which upon incorporation in a printing ink varnish can be used for printing on various substrates. The printing ink is distinguished by increased color strength, increased gloss and by a significantly improved flow behavior compared with a printing ink prepared without addition of the product from Preparation Example 2.

Similar results were obtained on using the compound according to the invention from Preparation Example 6.

Use Example 4 (comparative example)

44 parts of dinitroaniline were dissolved in the usual manner in 91 parts of 96% sulfuric acid, and the solution was introduced at 0° C. into 179.3 parts by volume of 34% hydrochloric acid. Diazotization was then carried out at the same temperature using 34.9 parts by volume of 40% aqueous sodium nitrite solution.

Pure β-naphthol was precipitated from a solution of 34.56 parts of β-naphthol in a mixture of 400 parts of water and 32 parts of 33% sodium hydroxide solution by dropwise addition of the solution to a mixture of 1200 parts of water and 40 parts of 31% hydrochloric acid.

The coupling reaction to give C.I. Pigment Orange 5 (C.I. No. 12075) was carried out in the usual manner by running in the clarified diazonium salt solution to the suspension of precipitated β-naphthol. The pigment was then filtered, washed with water and finally dried.

Use Example 4a

Use Example 4 was repeated, except that before the dropwise addition of the β-naphthol solution, another 4 parts of the compound according to the invention from Preparation Example 2 were added to the initial charge of 1200 parts of water and 40 parts of 31% hydrochloric acid.

The pigment thus obtained differs from the one prepared according to Use Example 4 by a clearly yellower shade and a substantially higher color strength not only in book and offset printing but also in aqueous preparations for flexographic printing or disperse dyes. The printing inks and preparations are distinguished by low viscosity. Moreover, the pigment thus obtained shows a higher gloss and better transparency in book and offset printing.

Use Example 5

138 parts of C.I. Pigment Red 112 (C.I. No. 12370) were milled together with 127 parts of a 35% aqueous solution of the compound according to Preparation Example 9 and 134 parts of water in a stirred ball mill in the presence of siliquartzite beads (1 mm in diameter), and the mill base obtained was then diluted by addition of 129 parts of water. The highly flowable pigment dispersion obtained in this manner is highly suitable for the dyeing and pigmenting of leather, for the standardization of gravure and flexographic printing inks and for the mass coloration of paper.

Use Example 6

138 parts of C.I. Pigment Brown 1 (C.I. No. 12480) were milled together with 125 parts of the compound according to the invention from Preparation Example 9 and 135 parts of water in a stirred ball mill in the presence of siliquartzite beads (1 mm in diameter), and the mill base was then diluted by addition of 129 parts of water. The readily flowable and stable pigment dispersion is suitable in particular for the dyeing and pigmenting of leather.

Use Example 7

138 parts of C.I. Pigment Yellow 83 (C.I. No. 21108) were milled analogously to Use Example 6 with 44 parts of a product obtainable by Preparation Example 11b and with 217 parts of water in a stirred ball mill in the presence of siliquartzite beads (1 mm in diameter), followed by workup. The pigment dispersion obtained has very good flowability, a long shelf life and is very suitable for use in book and offset printing or also for the dyeing and pigmenting of leather.

Use Example 8

100 parts of C.I. Sulfur Brown 51 (C.I. No. 53327) were milled analogously to Use Example 6 together with 229 parts of a 35% aqueous solution of the compound according to Preparation Example 9, and the mill base obtained was diluted with 71 parts of water. The pigment dispersion obtained is preferably suitable for the dyeing and pigmenting of leather by the surface dyeing and exhaust methods.

Use Example 9

50 parts of C.I. Disperse Orange 13 (C.I. No. 26080) were milled together with 85 parts of a product according to Preparation Example 9 and 65 parts of water in a stirred ball mill for 4 hours until fine dispersion was achieved. Addition of 50 parts of water gave a 20% color paste having very good fine dispersion which fulfills all coloristic requirements, in particular in the dyeing of yarns made of polyester, polyester/wool and polyester/staple viscose blends.

Use Example 10

70 parts of an aromatics-containing mineral oil were stirred together with 20 parts of the oleic ester according to Preparation Example 10b and 10 parts of the diethylenetriamine salt according to Preparation Example 2 until a homogeneous mixture was obtained, which was then diluted with water to 900 parts by volume. This gave a finely disperse to transparent mineral oil emulsion which, after being diluted 1:9, exhibits, apart from excellent stability over an extended period of time, also anticorrosive properties according to DIN (German Standard Specification) 51360 and can be used as coolant, for example, for metal cutting.

Use Example 11

70 parts of a purely aliphatic mineral oil were stirred together with 20 parts of a product according to Preparation Example 10b and 10 parts of a product according to Preparation Example 3b until a homogeneous mixture was obtained, which was then diluted with water to 900 parts by volume. This gave a finely disperse to transparent mineral oil emulsion which, after being diluted 1:10, exhibits, apart from excellent stability over an extended period of time, also anticorrosive properties according to DIN (German Standard Specification) 51360 and can be used as lubricant for continuous worsted yarn spinning.

Use Example 12

50 parts of the crop protection agent 2-carbomethoxyaminobenzimidazole were milled together with 68 parts of a 35% aqueous solution of the compound according to Preparation Example 9 and 82 parts of water in a high-speed 1-liter stirred pearl mill until fine dispersion was achieved. After the grinding medium had been separated off, a very stable dispersion having good suspending power without forming sediments is obtained. Similar results were obtained on using the compounds according to the invention from Preparation Example 4.

What is claimed is:

1. A compound of the formula (I)

$$[(Z)_{c1}-Y-CO-B-CO]_a-Y-(Z)_{c2} \quad (I)$$

in which
a is a number from 1 to 9;
c1 is the number 2 or 3;
c2 is the number 3;
each Y is a unit of the formula (Ia) which is identical to or different from that of the other Y radicals

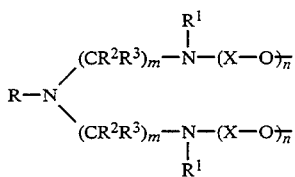

in which
X is selected from the group consisting of the formulae $-CH_2CH_2-$, $-CH(CH_3)CH_2-$ and $-CH_2-CH(CH_3)-$ or a combination thereof;
R is selected from the group consisting of a saturated straight-chain $C_{12}-C_{22}$-alkyl radical, unsaturated straight-chain $C_{12}-C_{22}$-alkyl radical, saturated branched $C_{12}-C_{22}$-alkyl radical and unsaturated branched $C_{12}-C_{22}$-alkyl radical,
$R^1$ is a hydrogen atom or a divalent group of the formula $-(X-O)_n-$,
$R^2$ and $R^3$ are identical or different and are a hydrogen atom or a methyl group,
m is a number from 2 to 3, and
each n is a number from 1 to 200 which can be identical to or different from that of the other n;
each Z is a radical selected from the group consisting of $Z^1$ to $Z^7$ which is identical to or different from that of the other Z, in which
$Z^1$ is hydrogen,
$Z^2$ is an acyl radical of a straight-chain, saturated or unsaturated $C_2-C_{22}$-carboxylic acid, which is unsubstituted or substituted by one or two hydroxyl groups,
$Z^3$ is an acyl radical of a dicarboxylic acid or tricarboxylic acid based on a dimerized $C_8-C_{24}$-fatty acid or trimerized $C_8-C_{24}$-fatty acid,
$Z^4$ is an acyl radical of the formula $R^4-CO-$, in which $R^4$ is selected from the group consisting of a phenyl, naphthyl, hydroxyphenyl and hydroxynaphthyl radical, $Z^5$ is an acyl radical of an unmodified or modified natural resin acid,
each $Z^6$ is a radical selected from the group consisting of $-CO-CH=CH-COOM$, $-CO-(CH_2)_q-COOM$, $-CO-CH_2-CH(SO_3M)-COOM$, $-CO-CH(SO_3M)-CH_2-COOM$, and $-CO-C_6H_4-COOM$ which is identical to or different from that of the other $Z^6$, in which q is an integer from 0 to 10, and
$Z^7$ is $-SO_3M$,
in which M is hydrogen; an alkali metal; one equivalent of an alkaline earth metal; and oxyalkyl radical of the formula $(X-O-)_nH$; an ammonium group which is unsubstituted or substituted by one to four $C_1-C_5$-alkyl radicals or one to four $C_2-C_5$-alkylol radicals; an ammonium group obtained from ammonia or from $C_1-C_5$-alkylamines or $C_2-C_5$-alkylolamines by an addition reaction with 1 to 150 ethylene oxide or propylene oxide units or a combination of ethylene oxide and propylene oxide units; or a group of the formula (II)

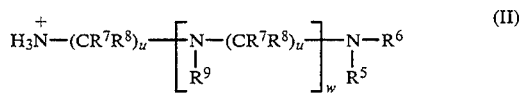

in which $R^9$, $R^5$ and $R^6$ are identical or different and are a hydrogen atom or a hydroxyalkyl group having 1 to 6 carbon atoms, and $R^7$ and $R^8$ are identical or different and are hydrogen or methyl, each u is identical to or different from the others and is an integer from 2 to 14, and w is an integer from zero to 25; or in which M is a group of the formula (III)

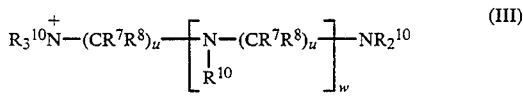

in which $R^{10}$ is the group $H-(O-X-)_y$, in which X has the abovementioned meanings and y is an integer from 1 to 100, and
B is a straight-chain, branched or cyclic aliphatic radical each having 1 to 60 carbon atoms, and is $C_6-C_2$-arylene or a group of the formula $-CH=CH-$, $-CH(SO_3M)CH_2-$ or $-CH_2CH(SO_3M)$, in which M is a cation or a radical of the formula $-(X-O-)_nH$.

2. A compound as claimed in claim 1, wherein a is a number from 1 to 4; and c1 and c2 are identical or different and are a number from 6 to 12.

3. A compound as claimed in claim 1, wherein
R is selected from the group consisting of a saturated straight-chain $C_{12}-C_{18}$-alkyl radical, unsaturated straight-chain $C_{12}-C_{18}$-alkyl radical, saturated branched $C_{12}-C_{18}$-alkyl radical and unsaturated branched $C_{12}-C_{18}$-alkyl radical;
all of the radicals are 50 to 100% of the formula $-CH_2-CH_2-$ and are 0 to 50% of the formula $-CH(CH_3)CH_2-$ or $-CH_2-CH(CH_3)-$;
B is selected from the group consisting of $C_1-C_6$-alkylene, 1,2-phenylene, 1,3-phenylene, 1,4-phenylene, a group of the formulae $-CH=CH-$, $-CH(SO_3M)CH_2-$ and $-CH_2CH(SO_3M)-$ in which M is a cation,
m is the number 3 and
n is a number from 1 to 50 which is identical to or different from that of the other.

4. A compound as claimed in claim 1, wherein

R is selected from the group consisting of a saturated straight-chain $C_{12}$–$C_{18}$-alkyl radical, unsaturated straight-chain $C_{12}$–$C_{18}$-alkyl radical, saturated branched $C_{12}$–$C_{18}$-alkyl radical and unsaturated branched $C_{12}$–$C_{18}$-alkyl radical;

80 to 100% of all of radicals X are a group of the formula —$CH_2$—$CH_2$— and 0 to 20% of all of the radicals X are a group of the formula —$CH(CH_3)CH_2$— or —$CH_2$—$CH(CH_3)$—;

B is selected from the group consisting of $C_1$-$C_6$-alkylene, 1,2-phenylene, 13-phenylene, 1,4-phenylene, a group of the formulae —CH=CH—, —CH($SO_3M$)$CH_2$— and —$CH_2CH(SO_3M)$— in which M is a cation, m is the number 3 and n is a number from 5 to 30 which is identical to or different from that of the other.

5. A compound as claimed in claim 1, wherein $R^2$ and $R^3$ are hydrogen atoms.

6. A compound as claimed in claim 1, wherein 20 to 100% of the radicals Z, in each case independently of one another, have the meaning of $Z^2$, $Z^3$, $Z^4$, $Z^5$, $Z^6$ or a combination thereof and 80 to 0% of the radicals Z have the meaning of $Z^1$, $Z^2$, $Z^4$, $Z^5$ or a combination thereof.

7. A compound as claimed in claim 1, wherein 30 to 70% of the radicals Z, in each case independently of one another, have the meaning of $Z^2$, $Z^3$, $Z^4$, $Z^5$, $Z^6$ or a combination thereof and 70 to 30% of the radicals Z have the meaning of $Z^1$, $Z^2$, $Z^4$, $Z^5$ or a combination thereof.

8. A compound as claimed in claim 1, wherein a is a number from 1 to 4 and Z has the meaning of $Z^1$.

9. A compound as claimed in claim 1, wherein the acid on which the acyl radical $Z^2$ is based is an even-numbered fatty acid or hydroxy fatty acid each having 8 to 20 carbon atoms.

10. A compound as claimed in claim 1, wherein the acid on which the acyl radical $Z^2$ is based is an even-numbered fatty acid or hydroxy fatty acid each having 12 to 18 carbon atoms.

11. A compound as claimed in claim 1, wherein the acid on which the acyl radical $Z^2$ is based is tall oil fatty acid, tallow fatty acid, coconut oil fatty acid, palm oil fatty acid, linseed oil fatty acid, castor oil fatty acid or ricenenic acid.

12. A compound as claimed in claim 1, wherein the acid on which the acyl radical $Z^4$ is based is benzoic acid, salicylic acid, o-methylbenzoic acid, m-methylbenzoic acid, p-methylbenzoic acid, naphthoic acid or hydroxynaphthoic acid.

13. A compound as claimed in claim 1, wherein the resin acid on which the acyl radical $Z^5$ is based is a resin acid which is present in commercially available rosin type, or is a rosin type.

14. A compound as claimed in claim 1, wherein the acid on which the acyl radical $Z^5$ is based is oxalic acid, malonic acid, succinic acid, glutaric acid, adipic acid, pimelic acid, suberic acid, azelaic acid, sebacic acid, phthalic acid, isophthalic acid, terephthalic acid, maleic acid, fumaric acid or sulfosuccinic acid.

15. A compound as claimed in claim 1, wherein M is hydrogen; an alkali metal; one equivalent of an alkaline earth metal; an ammonium group which is substituted by one to four $C_1$-$C_6$-alkyl radicals or one to four $C_2$-$C_5$-alkylol radicals; an ammonium group obtained from ammonia or from $C_1$-$C_5$-alkylamines or $C_2$-$C_5$-alkylolamines by an addition reaction with 5 to 30 ethylene oxide or propylene oxide units or a combination thereof; or a group of the formula (II)

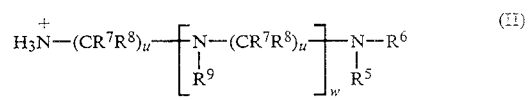

in which $R^9$, $R^5$ and $R^6$ are identical or different and are a hydrogen atom or a hydroxyalkyl group having 1 to 6 carbon atoms, and $R^7$ and $R^8$ are identical or different and are hydrogen or methyl, each u is identical to or different from the others and is an integer from 2 to 3, and w is an integer from zero to 5; or in which M is a group of the formula (III)

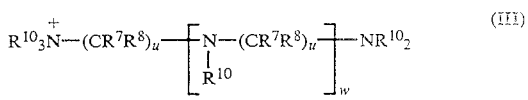

in which $R^{10}$ is the group H—(O—X—)$_y$, in which X has the abovementioned meanings and y is an integer from 1 to 30.

* * * * *